United States Patent
Gan et al.

(10) Patent No.: US 10,736,837 B2
(45) Date of Patent: *Aug. 11, 2020

(54) COMPOSITIONS FOR SENSITIVE SKIN

(71) Applicant: MARY KAY INC., Addison, TX (US)

(72) Inventors: David Gan, Southlake, TX (US); Tiffany Carle, Dallas, TX (US); Michelle Hines, Hickory Creek, TX (US); Milagros Sanchez, Dallas, TX (US); Patricia Jacoby, Dallas, TX (US); Linda Hart, Dallas, TX (US)

(73) Assignee: Mary Kay Inc., Addison, TX (US)

( * ) Notice: Subject to any disclaimer, the term of this patent is extended or adjusted under 35 U.S.C. 154(b) by 42 days.

This patent is subject to a terminal disclaimer.

(21) Appl. No.: 16/234,028

(22) Filed: Dec. 27, 2018

(65) Prior Publication Data

US 2019/0183786 A1    Jun. 20, 2019

Related U.S. Application Data

(63) Continuation of application No. 15/796,958, filed on Oct. 30, 2017, now Pat. No. 10,245,282, which is a continuation of application No. 14/550,664, filed on Nov. 21, 2014, now Pat. No. 9,801,900.

(60) Provisional application No. 61/907,836, filed on Nov. 22, 2013, provisional application No. 61/913,551, filed on Dec. 9, 2013, provisional application No. 61/921,803, filed on Dec. 30, 2013.

(51) Int. Cl.

| | | |
|---|---|---|
| *A61K 36/00* | (2006.01) | |
| *A61K 9/00* | (2006.01) | |
| *A61K 31/734* | (2006.01) | |
| *A61K 31/704* | (2006.01) | |
| *A61K 36/896* | (2006.01) | |
| *A61K 38/01* | (2006.01) | |
| *A61K 8/97* | (2017.01) | |
| *A61K 36/28* | (2006.01) | |
| *A61K 36/33* | (2006.01) | |
| *A61K 8/63* | (2006.01) | |
| *A61K 8/73* | (2006.01) | |
| *A61Q 19/00* | (2006.01) | |
| *A61K 8/9794* | (2017.01) | |
| *A61K 8/9789* | (2017.01) | |
| *A61K 8/64* | (2006.01) | |
| *A61K 9/06* | (2006.01) | |
| *A61K 9/107* | (2006.01) | |
| *A61K 36/23* | (2006.01) | |
| *A61K 36/88* | (2006.01) | |
| *A61K 38/16* | (2006.01) | |
| *A61Q 19/08* | (2006.01) | |

(52) U.S. Cl.
CPC .............. *A61K 9/0014* (2013.01); *A61K 8/63* (2013.01); *A61K 8/64* (2013.01); *A61K 8/73* (2013.01); *A61K 8/733* (2013.01); *A61K 8/97* (2013.01); *A61K 8/9789* (2017.08); *A61K 8/9794* (2017.08); *A61K 9/06* (2013.01); *A61K 9/107* (2013.01); *A61K 31/704* (2013.01); *A61K 31/734* (2013.01); *A61K 36/23* (2013.01); *A61K 36/28* (2013.01); *A61K 36/33* (2013.01); *A61K 36/88* (2013.01); *A61K 36/896* (2013.01); *A61K 38/011* (2013.01); *A61K 38/16* (2013.01); *A61Q 19/005* (2013.01); *A61Q 19/08* (2013.01)

(58) Field of Classification Search
CPC ....................................................... A61K 36/00
USPC ........................................................ 424/725
See application file for complete search history.

(56) References Cited

U.S. PATENT DOCUMENTS

| | | | |
|---|---|---|---|
| 2,798,053 | A | 7/1957 | Brown et al. |
| 3,755,560 | A | 8/1973 | Dickert et al. |
| 4,421,769 | A | 12/1983 | Dixon et al. |
| 4,509,949 | A | 4/1985 | Huang et al. |
| 4,599,379 | A | 7/1986 | Flesher et al. |
| 4,628,078 | A | 12/1986 | Glover et al. |
| 4,835,206 | A | 5/1989 | Farrar et al. |
| 4,849,484 | A | 7/1989 | Heard |
| 5,011,681 | A | 4/1991 | Ciotti et al. |
| 5,087,445 | A | 2/1992 | Haffey et al. |
| 5,100,660 | A | 3/1992 | Hawe et al. |
| 5,676,956 | A | 10/1997 | Duffy et al. |
| 6,664,225 | B2 | 12/2003 | Mumoli |
| 7,618,639 | B2 | 11/2009 | Olalde Rangel et al. |
| 7,993,645 | B2 | 8/2011 | Benson et al. |
| 7,993,654 | B2 | 8/2011 | Woeller et al. |
| 8,815,308 | B2 | 8/2014 | Florence et al. |
| 2005/0186290 | A1 | 8/2005 | Cals-Grierson |
| 2006/0051302 | A1 | 3/2006 | Jeanmarie et al. |
| 2009/0117061 | A1 | 5/2009 | Gross |
| 2009/0246163 | A1 | 10/2009 | Wahi |

(Continued)

FOREIGN PATENT DOCUMENTS

| | | |
|---|---|---|
| CN | 200810061519 | 11/2009 |
| CN | 201010221513 | 1/2012 |

(Continued)

OTHER PUBLICATIONS

International Cosmetic Ingredient Dictionary and Handbook, 12th Edition, 2008 ("CTFA"), vol. 1, p. 1211.
International Cosmetic Ingredient Dictionary and Handbook, 12th Edition, 2008 ("CTFA"), vol. 1, p. 940.

(Continued)

*Primary Examiner* — Michael V Meller
(74) *Attorney, Agent, or Firm* — Norton Rose Fulbright US LLP

(57) ABSTRACT

Disclosed are compositions and methods for their use that include a combination of hydrolyzed algin, escin, *Ruscus aculeatus* root extract, ammonium glycyrrhizate, *Centella asiatica* extract, hydrolyzed yeast protein, and *Calendula officinalis* flower extract.

14 Claims, No Drawings

(56) References Cited

U.S. PATENT DOCUMENTS

| | | | |
|---|---|---|---|
| 2010/0227830 | A1 | 9/2010 | Grassauer et al. |
| 2010/0297040 | A1 | 11/2010 | Keefe |
| 2011/0009352 | A1 | 1/2011 | Suzuki et al. |
| 2011/0015143 | A1 | 1/2011 | Mascolo et al. |
| 2011/0236324 | A1 | 9/2011 | Deo |
| 2011/0318285 | A1 | 12/2011 | Erazo-Majewicz et al. |
| 2012/0027697 | A1 | 2/2012 | Deo |
| 2012/0237540 | A1 | 9/2012 | Florence et al. |
| 2012/0276025 | A1 | 11/2012 | Florence et al. |
| 2013/0183358 | A1 | 7/2013 | Fernandez et al. |

FOREIGN PATENT DOCUMENTS

| | | |
|---|---|---|
| CN | 201010237906 | 2/2012 |
| CN | 103284897 | 9/2013 |
| WO | WO 1997/36571 | 10/1997 |
| WO | WO 2011/103449 | 8/2011 |
| WO | WO 2011/161465 | 12/2011 |
| WO | WO 2012/072951 | 6/2012 |

OTHER PUBLICATIONS

International Cosmetic Ingredient Dictionary and Handbook, 12th Edition, 2008 ("CTFA"), vol. 2, p. 2405.
International Cosmetic Ingredient Dictionary and Handbook, $12^{th}$ Edition, 2008 ("CTFA"), vol. 1, p. 154.
International Cosmetic Ingredient Dictionary and Handbook, 12th Edition, 2008 ("CTFA"), vol. 1, p. 458-460.
International Cosmetic Ingredient Dictionary and Handbook, $12^{th}$ Edition, 2008 ("CTFA"), vol. 1, p. 1242.
International Cosmetic Ingredient Dictionary and Handbook, $12^{th}$ Edition, 2008 ("CTFA"), vol. 1, p. 388-390.
International Cosmetic Ingredient Dictionary and Handbook, $4^{th}$ Edition, 1991 ("CTFA"), p. 12 and 80.
CTFA International Cosmetic Ingredient Dictionary and Handbook (2004 and 2008).
International Search Report and Written Opinion issued in PCT/US2014/066910 dated Feb. 25, 2015
"BASF Biophytex™ Visibly improved skin complexion and a younger, healthier appearance" *BASF Beauty Creations*, 2012.
"Hygienic Standards for Cosmetics" *The PRC Hygiene Ministry: Limited Preservatives in Cosmetic Compositions*. 2007. (English translation provided).

COMPOSITIONS FOR SENSITIVE SKIN

CROSS REFERENCE TO RELATED APPLICATIONS

This application is a continuation of U.S. application Ser. No. 15/796,958, filed Oct. 30, 2017, which is a continuation of U.S. application Ser. No. 14/550,664, filed Nov. 21, 2014, which claims the benefit of U.S. Provisional Application No. 61/921,803, filed Dec. 30, 2013, U.S. Provisional Application No. 61/913,551, filed Dec. 9, 2013, and U.S. Provisional Application No. 61/907,836, filed Nov. 22, 2013. The contents of the referenced applications are incorporated into the present application by reference.

BACKGROUND OF THE INVENTION

A. Field of the Invention

The present invention relates to a combination of ingredients that can be used to treat or prevent erythema (i.e., reddened/flushed skin) in people having sensitive skin. This combination of ingredients can be included in a wide-range of product formulations (e.g., toners, gels, masks, etc.).

B. Description of Related Art

Sensitive skin is a condition where the skin has a tendency towards flushing, reddening, or blushing (i.e., erythema) when exposed to stimuli such as UV light, heat, cold, chemicals, or active ingredients in skin formulations, etc. One of the issues in the cosmetics industry is that active ingredients known to potentially cause erythema in sensitive skin are needed to treat a given skin condition such as fine lines and wrinkles, sagging skin, acne, etc. Therefore, people with sensitive skin either have to avoid such products or end up purchasing additional products that can help alleviate the aforementioned symptoms associated with sensitive skin.

SUMMARY OF THE INVENTION

The present invention offers a solution to the aforementioned problems. The solution is premised on a discovery of a combination of ingredients—hydrolyzed algin, escin, *Ruscus aculeatus* root extract, ammonium glycyrrhizate, *Centella asiatica* extract, hydrolyzed yeast protein, and *Calendula officinalis* flower extract—that can be used to alleviate or even prevent symptoms associated with sensitive skin (e.g., erythema or skin inflammation). This combination of ingredients can be used in a variety of product formulations (e.g., toners, cleansers, emulsions such as lotions or creams, masks, gels, etc.) along with other skin-active ingredients that are known to cause erythema when applied to sensitive skin. That is to say, this combination of ingredients can be used with other known skin-active ingredients so as to treat a given skin condition (e.g., with the known skin active) and prevent or reduce the symptoms associated with sensitive skin (e.g., with the aforementioned combination of ingredients). Without wishing to be bound by theory, it is believed that the discovered combination of ingredients provides for a strong anti-oxidative effect (see Examples) and/or which interferes with various steps in the inflammatory process/cascade, thereby reducing the flushing/blushing/reddening that is typically seen with sensitive skin.

In one instance, there is disclosed a topical skin composition comprising a combination of hydrolyzed algin, escin, *Ruscus aculeatus* root extract, ammonium glycyrrhizate, *Centella asiatica* extract, hydrolyzed yeast protein, and *Calendula officinalis* flower extract. Alternatively, an one or any combination said ingredients can be used in the compositions of the present invention. For instance, a combination of escin, *Ruscus aculeatus* root extract, ammonium glycyrrhizate, *Centella asiatica* extract, hydrolyzed yeast protein, and *Calendula officinalis* flower extract can be used as an anti-oxidant on skin in need of an anti-oxidant. The amounts of the ingredients within the composition can vary (e.g., amounts can be as low as 0.000001% to as high as 60% w/w or any ranger therein). In one instance, the composition includes 0.0001% to 1% w/w of escin, 0.0001% to 1% w/w of *Ruscus aculeatus* root extract, 0.0001% to 1% w/w of ammonium glycyrrhizate, 0.0001% to 1% w/w of *Centella asiatica* extract, 0.0001% to 1% w/w of hydrolyzed yeast protein, and 0.0001% to 1% w/w of *Calendula officinalis* flower extract and can also include 0.0001% to 1% w/w of hydrolyzed algin. In some aspects, disclosed are methods of applying any of the topical skin compositions disclosed herein comprising applying said composition to skin. In some aspects, the composition is applied to sensitive skin.

In another aspect, there is disclosed a topical skin composition formulated as a toner comprising any one of, any combination of, or all of escin, *Ruscus aculeatus* root extract, ammonium glycyrrhizate, *Centella asiatica* extract, hydrolyzed yeast protein, *Calendula officinalis* flower extract, water, butylene glycol, glycerin, propylene glycol, diazolidinyl urea, PPG-5-ceteth-20, methylparaben, sodium citrate, disodium EDTA, buteth-3, propylparaben, citric acid, sodium benzotriazolyl butylphenol sulfonate, panthenol, hydrolyzed algin, sodium hyaluronate, simethicone, tributyl citrate, phenoxyethanol, cyclotetrasiloxane, potassium sorbate, sodium benzoate, cyclopentasiloxane, cyclohexasiloxane, and *Opuntia tuna* fruit extract. The amounts of the ingredients within the composition can vary (e.g., amounts can be as low as 0.000001% to as high as 60% w/w or any ranger therein). In one instance, the composition includes 0.0001% to 1% w/w of escin, 0.0001% to 1% w/w of *Ruscus aculeatus* root extract, 0.0001% to 1% w/w of ammonium glycyrrhizate, 0.0001% to 1% w/w of *Centella asiatica* extract, 0.0001% to 1% w/w of hydrolyzed yeast protein, 0.0001% to 1% w/w of *Calendula officinalis* flower extract, 70% to 90% w/w of water, 5% to 7% w/w of butylene glycol, 3% to 6% w/w of glycerin, 0.1% to 1.0% w/w of propylene glycol, 0.1% to 0.5% w/w of diazolidinyl urea, 0.01% to 0.3% w/w of PPG-5-ceteth-20, 0.05% to 0.5% w/w of methylparaben, 0.05% to 0.5% w/w of sodium citrate, 0.05% to 0.5% w/w of disodium EDTA, 0.005% to 0.05% w/w of buteth-3, 0.005% to 0.05% w/w of propylparaben, 0.005% to 0.05% w/w of citric acid, 0.005% to 0.05% w/w of sodium benzotriazolyl butylphenol sulfonate, 0.005% to 0.05% w/w of panthenol, 0.001% to 0.01% w/w of hydrolyzed algin, 0.001% to 0.01% w/w of sodium hyaluronate, 0.0001% to 0.001% w/w of simethicone, 0.0001% to 0.001% w/w of tributyl citrate, 0.0001% to 0.001% w/w of phenoxyethanol, 0.0001% to 0.001% w/w of cyclotetrasiloxane, 0.0001% to 0.001% w/w of potassium sorbate, 0.0001% to 0.001% w/w of sodium benzoate, 0.0001% to 0.001% w/w of cyclopentasiloxane, 0.0001% to 0.001% w/w of cyclohexasiloxane, and 0.0001% to 0.1% w/w of *Opuntia tuna* fruit extract. In some aspects, also disclosed are methods of applying the disclosed compositions to skin within 5 minutes after the skin has been cleansed by a cleansing composition. In some aspects, a moisturizer is applied to skin within 5 minutes after applying any one of these topical skin compositions to skin.

In another aspect, there is disclosed a topical skin composition formulated as a mask comprising any one of, any combination of, or all of escin, *Ruscus aculeatus* root extract, ammonium glycyrrhizate, *Centella asiatica* extract, hydrolyzed yeast protein, *Calendula officinalis* flower extract, water, pentylene glycol, polysilicone-11, hydroxyethyl acrylate/sodium acryloyldimethyl taurate copolymer, dimethicone, squalane, glyceryl undecylenate, benzyl alcohol, silica, butylene glycol, triethanolamine, polysorbate 60, acrylates/C10-30 alkyl acrylate crosspolymer, hydroxypropyl cyclodextrin, sorbitan isostearate, panthenol, hydrolyzed algin, glycerin, iodopropynyl butylcarbamate, phenoxyethanol, sodium citrate, sodium benzoate, citric acid, potassium sorbate, and *Opuntia tuna* fruit extract. The amounts of the ingredients within the composition can vary (e.g., amounts can be as low as 0.000001% to as high as 60% w/w or any ranger therein). In one instance, the composition includes 0.0001% to 1% w/w of escin, 0.0001% to 1% w/w of *Ruscus aculeatus* root extract, 0.0001% to 1% w/w of ammonium glycyrrhizate, 0.0001% to 1% w/w of *Centella asiatica* extract, 0.0001% to 1% w/w of hydrolyzed yeast protein, 0.0001% to 1% w/w of *Calendula officinalis* flower extract, 75% to 95% w/w of water, 4% to 6% w/w of pentylene glycol, 1% to 4% w/w of polysilicone-11, 1% to 3% w/w of hydroxyethyl acrylate/sodium acryloyldimethyl taurate copolymer, 1% to 3% w/w of dimethicone, 1% to 3% w/w of squalane, 0.5% to 1.5% w/w of glyceryl undecylenate, 0.5% to 1.5% w/w of benzyl alcohol, 0.1% to 1.0% w/w of silica, 0.1% to 1.0% w/w of butylene glycol, 0.1% to 1.0% w/w of triethanolamine, 0.1% to 1.0% w/w of polysorbate 60, 0.1% to 1.0% w/w of acrylates/C10-30 alkyl acrylate crosspolymer, 0.01% to 0.1% w/w of hydroxypropyl cyclodextrin, 0.01% to 0.1% w/w of sorbitan isostearate, 0.01% to 0.1% w/w of panthenol, 0.01% to 0.1% w/w of hydrolyzed algin, 0.01% to 0.1% w/w of glycerin, 0.001% to 0.1% w/w of iodopropynyl butylcarbamate, 0.001% to 0.1% w/w of phenoxyethanol, 0.0001% to 0.001% w/w of sodium citrate, 0.0001% to 0.001% w/w of sodium benzoate, 0.0001% to 0.001% w/w of citric acid, and 0.0001% to 0.001% w/w of potassium sorbate. In some aspects, also disclosed are methods of applying any one of the topical skin compositions of disclosed herein to skin comprising applying said composition to skin, wherein the composition remains on the skin for 1 to 12 hours.

In another aspect, there is disclosed a topical skin composition formulated as a cream or gel capable of reducing the appearance of dark circles or puffy eyes comprising any one of, any combination of, or all of hydrolyzed align, escin, *Ruscus aculeatus* root extract, ammonium glycyrrhizate, *Centella asiatica* extract, hydrolyzed yeast protein, *Calendula officinalis* flower extract, water, glycerin, pentylene glycol, glycereth-26, propylene glycol, triethanolamine, acrylates/C10-30 alkyl acrylate crosspolymer, diazolidinyl urea, hydroxyethylcellulose, sodium polyacrylate, methylparaben, disodium EDTA, butylene glycol, phenoxyethanol, caprylyl glycol, propylparaben, panthenol, and *Opuntia tuna* fruit extract. The amounts of the ingredients within the composition can vary (e.g., amounts can be as low as 0.000001% to as high as 60% w/w or any ranger therein). In one instance, the composition includes 0.005% to 0.05% w/w of hydrolyzed align, 0.0001% to 1% w/w of escin, 0.0001% to 1% w/w of *Ruscus aculeatus* root extract, 0.0001% to 1% w/w of ammonium glycyrrhizate, 0.0001% to 1% w/w of *Centella asiatica* extract, 0.0001% to 1% w/w of hydrolyzed yeast protein, 0.0001% to 1% w/w of *Calendula officinalis* flower extract, 75% to 95% w/w of water, 3 to 7% by weight of glycerin, 3 to 7% by weight of pentylene glycol, 1 to 3% by weight of glycereth-26, 0.3 to 0.7% by weight of propylene glycol, 0.3 to 0.7% by weight of triethanolamine, 0.1 to 0.5% by weight of acrylates/C10-30 alkyl acrylate crosspolymer, 0.1 to 0.5% by weight of diazolidinyl urea, 0.1 to 0.5% by weight of hydroxyethylcellulose, 0.1 to 0.5% by weight of sodium polyacrylate, 0.1 to 0.5% by weight of methylparaben, 0.05 to 0.5% by weight of disodium EDTA, 0.05 to 0.1% by weight of butylene glycol, 0.03 to 0.07% by weight of phenoxyethanol, 0.03 to 0.07% by weight of caprylyl glycol, 0.01 to 0.05% by weight of propylparaben, and, 0.01 to 0.05% by weight of panthenol.

In yet another aspect, there is disclosed a topical skin composition formulated as a cream or gel capable of reducing the appearance of dark circles or puffy eyes comprising any one of, any combination of, or all of escin, *Ruscus aculeatus* root extract, ammonium glycyrrhizate, *Centella asiatica* extract, hydrolyzed yeast protein, *Calendula officinalis* flower extract, water, glycerin, pentylene glycol, glycereth-26, benzyl alcohol, triethanolamine, acrylates/C10-30 alkyl acrylate crosspolymer, hydroxyethylcellulose, sodium polyacrylate, disodium EDTA, hydroxypropyl cyclodextrin, butylene glycol, phenoxyethanol, caprylyl glycol, panthenol, iodopropynyl butylcarbamate, hydrolyzed algin, mica, titanium dioxide, sodium citrate, potassium sorbate, sodium benzoate, citric acid, and *Opuntia tuna* fruit extract. The amounts of the ingredients within the composition can vary (e.g., amounts can be as low as 0.000001% to as high as 60% w/w or any ranger therein). In one instance, the composition includes 0.0001% to 1% w/w of escin, 0.0001% to 1% w/w of *Ruscus aculeatus* root extract, 0.0001% to 1% w/w of ammonium glycyrrhizate, 0.0001% to 1% w/w of *Centella asiatica* extract, 0.0001% to 1% w/w of hydrolyzed yeast protein, 0.0001% to 1% w/w of *Calendula officinalis* flower extract, 75% to 95% w/w of water, 3% to 7% w/w of glycerin, 2% to 5% w/w of pentylene glycol, 1% to 3% w/w of glycereth-26, 0.3% to 1.5% w/w of benzyl alcohol, 0.1% to 1.5% w/w of triethanolamine, 0.1% to 0.7% w/w of acrylates/C10-30 alkyl acrylate crosspolymer, 0.01% to 1.0% w/w of hydroxyethylcellulose, 0.01% to 1.0% w/w of sodium polyacrylate, 0.01% to 1.0% w/w of disodium EDTA, 0.01% to 1.0% w/w of hydroxypropyl cyclodextrin, 0.01% to 1.0% w/w of butylene glycol, 0.01% to 1.0% w/w of phenoxyethanol, 0.01% to 0.1% w/w of caprylyl glycol, 0.005% to 0.1% w/w of panthenol, 0.001% to 0.03% w/w of iodopropynyl butylcarbamate, 0.001% to 0.003% w/w of hydrolyzed algin, 0.001% to 0.03% w/w of mica, 0.001% to 0.03% w/w of titanium dioxide, 0.0001% to 0.0003% w/w of sodium citrate, 0.0001% to 0.0003% w/w of potassium sorbate, 0.0001% to 0.0003% w/w of sodium benzoate, and 0.0001% to 0.0003% w/w of citric acid.

Also contemplated are methods of treating erythemic skin or erythema comprising topically applying any of the aforementioned compositions to skin that has or is likely to develop erythema. Skin likely to develop erythema includes people that have sensitive skin. Erythema typically results from an increase in blood flow to the surface of the skin. The compositions can also be used to treat skin inflammation by reducing TNF-α, IL-6, IL-8, IL-10, IL-12 p40, GM-CSF cytokine production, and/or CGRP production in the skin. The compositions can also be used as an antioxidant to treat a wide range of skin conditions such as fine lines, wrinkles, sagging skin. For instance, the anti-oxidative effects of the combination of ingredients can be used to prevent or reduce the formation of reactive oxygen species (ROS) or can prevent ROS from interacting with cellular mechanisms within the skin.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Also disclosed in the context of the present invention are Embodiments 1 to 22. Embodiment 1 is a topical skin composition comprising an effective amount of hydrolyzed algin, escin, *Ruscus aculeatus* root extract, ammonium glycyrrhizate, *Centella asiatica* extract, hydrolyzed yeast protein, and *Calendula officinalis* flower extract, wherein the composition is capable of reducing cytokine production and reducing oxidative damage in skin cells. Embodiment 2 is the topical skin composition of Embodiment 1, further comprising between 80 to 90% by weight of water. Embodiment 3 is the topical skin composition of Embodiment 2, comprising 0.005 to 0.05% by weight of hydrolyzed algin. Embodiment 4 is the topical skin composition of Embodiment 3, comprising 0.001 to 0.05% by weight of escin, 0.001 to 0.01% by weight of *Ruscus aculeatus* root extract, 0.001 to 0.01% by weight of ammonium glycyrrhizate, 0.0005 to 0.005% by weight of *Centella asiatica* extract, 0.0003 to 0.003% by weight of hydrolyzed yeast protein, and 0.0003 to 0.003% by weight of *Calendula officinalis* flower extract. Embodiment 5 is the topical skin composition of Embodiment 3, further comprising *Opuntia tuna* fruit extract. Embodiment 6 is the topical skin composition of any one of Embodiments 1 to 5, wherein the composition further includes: butylene glycol; glycerin; propylene glycol; diazolidinyl urea; PPG-5-ceteth-20; methylparaben; sodium citrate; disodium EDTA; buteth-3; propylparaben; citric acid; sodium benzotriazolyl butylphenol sulfonate; and panthenol. Embodiment 7 is the topical skin composition of Embodiment 6, wherein the composition includes: 5 to 7% by weight of butylene glycol; 3 to 5% by weight of glycerin; 0.3 to 0.7% by weight of propylene glycol; 0.1 to 0.5% by weight of diazolidinyl urea; 0.1 to 0.5% by weight of PPG-5-ceteth-20; 0.1 to 0.5% by weight of methylparaben; 0.05 to 0.1% by weight of sodium citrate; 0.03 to 0.07% by weight of disodium EDTA; 0.03 to 0.07% by weight of buteth-3; 0.01 to 0.05% by weight of propylparaben; 0.01 to 0.05% by weight of citric acid; 0.01 to 0.05% by weight of sodium benzotriazolyl butylphenol sulfonate; and 0.01 to 0.05% by weight of panthenol. Embodiment 8 is the topical skin composition of any one of Embodiments 1 to 5, wherein the composition further includes: glycerin; pentylene glycol; glycereth-26; propylene glycol; triethanolamine; acrylates/C10-30 alkyl acrylate crosspolymer; diazolidinyl urea; hydroxyethylcellulose; sodium polyacrylate; methylparaben; disodium EDTA; butylene glycol; phenoxyethanol; caprylyl glycol; propylparaben; and panthenol. Embodiment 9 is the topical skin composition of Embodiment 8, wherein the composition includes: 3 to 7% by weight of glycerin; 3 to 7% by weight of pentylene glycol; 1 to 3% by weight of glycereth-26; 0.3 to 0.7% by weight of propylene glycol; 0.3 to 0.7% by weight of triethanolamine; 0.1 to 0.5% by weight of acrylates/C10-30 alkyl acrylate crosspolymer; 0.1 to 0.5% by weight of diazolidinyl urea; 0.1 to 0.5% by weight of hydroxyethylcellulose; 0.1 to 0.5% by weight of sodium polyacrylate; 0.1 to 0.5% by weight of methylparaben; 0.05 to 0.5% by weight of disodium EDTA; 0.05 to 0.1% by weight of butylene glycol; 0.03 to 0.07% by weight of phenoxyethanol; 0.03 to 0.07% by weight of caprylyl glycol; 0.01 to 0.05% by weight of propylparaben; and 0.01 to 0.05% by weight of panthenol. Embodiment 10 is the topical skin composition of any one of Embodiments 1 to 5, wherein the composition further includes: pentylene glycol; polysilicone-11; hydroxyethyl acrylate/sodium acryloyldimethyl taurate copolymer; dimethicone; squalane; glyceryl undecylenate; silica; butylene glycol; triethanolamine; polysorbate 60; acrylates/C10-30 alkyl acrylate crosspolymer; hydroxypropyl cyclodextrin; sorbitan isostearate; panthenol; and glycerin. Embodiment 11 is the topical skin composition of Embodiment 10, wherein the composition includes: 3 to 7% by weight of pentylene glycol; 1 to 5% by weight of polysilicone-11; 1 to 5% by weight of hydroxyethyl acrylate/sodium acryloyldimethyl taurate copolymer; 1 to 3% by weight of dimethicone; 1 to 3% by weight of squalane; 0.5 to 2% by weight of glyceryl undecylenate; 0.3 to 0.7% by weight of silica; 0.1 to 0.5% by weight of butylene glycol; 0.1 to 0.5% by weight of triethanolamine; 0.1 to 0.5% by weight of polysorbate 60; 0.1 to 0.5% by weight of acrylates/C10-30 alkyl acrylate crosspolymer; 0.05 to 0.1% by weight of hydroxypropyl cyclodextrin; 0.05 to 0.1% by weight of sorbitan isostearate; 0.03 to 0.07% by weight of panthenol; and 0.03 to 0.07% by weight of glycerin. Embodiment 12 is the topical skin composition of Embodiment 11, wherein the composition further includes benzyl alcohol. Embodiment 13 is the topical skin composition of Embodiment 12, wherein the composition includes 0.1 to 1% by weight of benzyl alcohol. Embodiment 14 is the topical skin composition of any one of Embodiments 1 to 5, wherein the composition further includes: glycerin; pentylene glycol; glycereth-26; benzyl alcohol; triethanolamine; acrylates/C10-30 alkyl acrylate crosspolymer; hydroxyethylcellulose; sodium polyacrylate; disodium EDTA; hydroxypropyl cyclodextrin; butylene glycol; phenoxyethanol; caprylyl glycol; and panthenol. Embodiment 15 is the topical skin composition of Embodiment 14, wherein the composition includes: 3 to 7% by weight of glycerin; 2 to 5% by weight of pentylene glycol; 1 to 3% by weight of glycereth-26; 0.3 to 1.5% by weight of benzyl alcohol; 0.1 to 1.5% by weight of triethanolamine; 0.1 to 0.7% by weight of acrylates/C10-30 alkyl acrylate crosspolymer; 0.01 to 1.0% by weight of hydroxyethylcellulose; 0.01 to 1.0% by weight of sodium polyacrylate; 0.01 to 1.0% by weight of disodium EDTA; 0.01 to 1.0% by weight of hydroxypropyl cyclodextrin; 0.01 to 1.0% by weight of butylene glycol; 0.01 to 1.0% by weight of phenoxyethanol; 0.01 to 0.1% by weight of caprylyl glycol; and 0.005 to 0.1% by weight of panthenol. Embodiment 16 is a method of reducing pro-inflammatory cytokine production in skin cells and protecting skin from oxidative damage from free radicals comprising topically applying the composition of any one of Embodiments 1 to 15 to skin in need thereof, wherein said composition reduces pro-inflammatory cytokine production in skin cells and protects skin from oxidative damage from free radicals. Embodiment 17 is the method of Embodiment 16, wherein the pro-inflammatory cytokine is TNF-α, IL-6, IL-8, IL-10, IL-12 p40, or GM-CSF, or any combination or all thereof. Embodiment 18 is the method of Embodiment 17, wherein the composition is applied to erythemic, sensitive, or inflamed skin. Embodiment 19 is the method of Embodiment 17, wherein the composition is applied to dry, flaky, or itchy skin. Embodiment 20 is a method of reducing CGRP production in skin cells and protecting skin from oxidative damage from free radicals comprising topically applying the composition of any one of Embodiments 1 to 15 to skin in need thereof, wherein said composition reduces CGRP production in skin cells and protects skin from oxidative damage from free radicals. Embodiment 21 is the method of Embodiment 20, wherein the composition is applied to erythemic, sensitive, or inflamed skin. Embodiment 22 is the method of Embodiment 20, wherein the composition is applied to dry, flaky, or itchy skin.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse of composition can be a skin cleanser, shampoo, conditioner, or soap. An example of a leave-on composition can be a skin moisturizer, sunscreen, mask, overnight cream, or a day cream.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the compositions' abilities to reduce or prevent symptoms associated with sensitive skin (e.g., erythema) from appearing on a user's skin.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

People afflicted with sensitive skin are susceptible to skin reactions with current products on the market that include active ingredients targeted towards a specific skin condition such as fine lines and wrinkles, loss of elasticity, hyperpigmentation, melasma, dry skin, oily skin, acne, etc. While treatment of a particular skin condition can be beneficial, it can also result in adverse effects such as producing reddened or inflamed skin in people that have sensitive skin. The present invention offers a solution to this problem by providing a combination of ingredients that can be used on sensitive skin without producing a skin-irritating reaction such as erythema/reddening of the skin.

These and other non-limiting aspects of the present invention are provided in the following subsections.

A. Combination of Ingredients

The present invention is premised on a discovery of a combination of ingredients—hydrolyzed algin, escin, *Ruscus aculeatus* root extract, ammonium glycyrrhizate, *Centella asiatica* extract, hydrolyzed yeast protein, and *Calendula officinalis* flower extract—that can be used to alleviate or even prevent symptoms associated with sensitive skin. These ingredients are discussed in more detail below.

Hydrolyzed algin is a hydrolysate of algin. This ingredient is commercially available from a variety of sources (see, e.g., CTFA, Volume 1, page 1211, which is incorporated by reference). An exemplary source can be obtained from Barnet Products Corporation under the trade name Phyko-Al-PF. It has been discovered that this ingredient can be used to reduce the production of a variety of pro-inflammatory cytokines and CGRP production (See Example 1).

Escin, also known as aescin, is a mixture of saponins found in the seed of *Aesculus hippocastanum* (the horse chestnut). This active ingredient is commercially available from a variety of sources (see, e.g., International Cosmetic Ingredient Dictionary and Handbook, 12$^{th}$ Edition, 2008 ("CTFA"), Volume 1, page 940, which is incorporated by reference).

*Ruscus aculeatus* root extract is an extract from the root of a low evergreen Eurasian shrub in the Asparagaceae family. It is native to northern European and Eurasian countries. This extract is commercially available from a variety of sources (see, e.g., CTFA, Volume 2, page 2405, which is incorporated by reference). In some embodiments, the extract can be an aqueous, alcoholic, or hydro-alcoholic extract.

Ammonium glycyrrhizate is an ammonium salt of glycyrrhizic acid, and is commercially available from a variety of sources (see, e.g., CTFA, Volume 1, page 154, which is incorporated by reference).

The *Centella asiatica* plant is a small herbaceous plant that is native to countries such as India, Sri Lanka, Australia, Indonesia, Malaysia, Melanesia, Papua New Guinea, and other parts of Asia. Extracts from this plant are commercially available from a wide range of sources (see, e.g., CTFA, Volume 1, pages 458-60, which is incorporated by reference). In particular embodiments, the whole plant extract can be used (see pages 458-59 of the CTFA). An exemplary source can be obtained from Bayer Sante Familiale SAS (France) under the trade name TECA (Titrated Extract of *Centella asiatica*), which includes asiaticoside, madecassic acid, and asiatic acid. In some embodiments, the extract can be an aqueous, alcoholic, or hydro-alcoholic extract.

Hydrolyzed yeast protein is a hydrolysate of yeast proteins. This active ingredient is commercially available from a variety of sources (see, e.g., CTFA, Volume 1, page 1242, which is incorporated by reference).

*Calendula officinalis* flower extract is an extract of the Calendula (*Calendula officinalis*) flowers. The plant is native to central, eastern and southern Europe. It is commercially available from a wide variety of sources (see, e.g., CTFA, Volume 1, pages 388-390, which is incorporated by reference). In some embodiments, the extract can be an aqueous, alcoholic, or hydro-alcoholic extract.

Additionally, a blend of escin, *Ruscus aculeatus* root extract, ammonium glycyrrhizate, *Centella asiatica* extract, hydrolyzed yeast protein, and *Calendula officinalis* flower extract can be purchased under the trade name Biphytex™ LS 9832 from BASF Care Creations. It has been discovered that this blend can be used as an anti-oxidant (See Example 1). The blend can be used in amounts ranging from 0.01 to 2% by weight.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can be incorporated into all types of vehicles. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments. Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

D. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. *Aloe vera*, chamomile, cucumber extract, Ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., *Aloe* extracts, allantoin, bisabolol, ceramides, dimethicone, hyaluronic acid, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, *Aloe barbadensis*, *Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (Oenothera biennis) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, macadamia ternifolia nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antip soriatic agents, anti seborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

E. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Efficacy of Ingredients

Inhibition of Pro-Inflammatory Cytokines

Hydrolyzed algin was found to inhibit production of a variety of pro-inflammatory cytokines in primary adult human keratinocytes (Cascade # C-005-5C) using a MesoScale Discovery SECTOR Imager 2400. The Imager 2400 was used to detect and calculate the amount of a selected pro-inflammatory cytokine present in a sample. A summary of these data are provided in Table 1.

TABLE 1*

| Pro-Inflammatory Cytokine | % Change From Control** |
| --- | --- |
| TNF-α | −37 |
| IL-6 | −70 |
| IL-8 | −33 |
| IL-10 | −40 |
| IL-12 p40 | −32 |
| GM-CSF | −28 |

*1% hydrolyzed algin was used and was obtained from Barnet Products Corporation under the trade name Phyko-AL-PF.
**Control used was 0.5% DMSO. % Change From Control = % Pro-inflammatory Cytokine − % Pro-Inflammatory Cytokine of Control. Therefore, a negative (−) indicates inhibition of cytokine production.

The procedure used to obtain the data in Table 1 included the following steps:

Cell Culture—HEKa: HEKa cells were grown to subconfluence from a frozen vial in 3×T75 tissue culture flasks (37° C., 5% CO2). Confluent T75s (P1-P3) were washed with HBSS then trypsinized with 1.5 ml trypsin for ~4 min at 37° C. Cells were collected in 4 ml TNS, then spin in 15 ml conical tubes and resuspended in Epilife media and plate in 6 well dishes. Test compounds were diluted to 1% and 0.1% in media+10 ng/ml PMA. Upon reaching 85% confluence, the cells were washed and the media was replaced with 2 ml diluted test compound for 4-6 hrs (37° C., 5% CO2). 2 ml media was collected from each well, aliquot, and freeze at −80° C. until assayed with Procollagen peptide kit (PIP). All media was removed from cells, and 1 mL diluted MTS reagent was added to each well, incubated for 15-30 min (37° C., 5% CO2), and the plate was read at 490 nm.

Step 1: Samples may not require dilution prior to use in the assay. Bring appropriate diluents and plates to room temperature and thaw cytokine calibrators on ice. Store detection antibody mix at 4° C.; shield from light. Prepare calibrator solutions and calibration curve. (If applicable). Use the 1 μg/mL calibrator stock to prepare an 8-point calibration curve of 10,000, 2500, 625, 156, 39, 9.8, 2.4, and 0 pg/mL. The calibration curve can be modified as necessary to meet specific assay requirements. Prepare Detection Antibody Solution by diluting the Detection Antibody to 1 μg/mL in 3.0 mL of HSC. Antibody Diluent (per plate) (serum/plasma samples), or Antibody Diluent (tissue culture samples). Keep this reagent in the dark. Prepare 25 mL of 2× Read Buffer T by diluting 4× Read Buffer T 1:2 with deionized water. Continue with assay using appropriate protocol below.

Step 2: For MULTI-SPOT Assays with IFN-γ, Dispense 150 μL/well 1% Blocker B Solution. For MULTI-SPOT Assays with IL-12p40, dispense 150 μL/well 0.1% Blocker B Solution. Incubate at room temperature with vigorous shaking (300-1000 rpm) for 1 hour. Wash plate 3× with PBS or other standard buffer. Dispense 25 μL/well Calibrator or Sample. Incubate at room temperature with vigorous shaking (300-1000 rpm) for 1-2 hours.

Step 3: Dispense 25 μL/well 1 μg/mL Detection Antibody Solution. Incubate at room temperature with vigorous shaking (300-1000 rpm) for 1-2 hours.

Step 4: Wash plate 3× with PBS-0.05% Tween-20. Dispense 150 μL/well 2× Read Buffer T. Analyze plate on SECTOR Imager 2400 instrument.

Inhibition of CGRP Production

Hydrolyzed algin was found to inhibit production of CGRP by human epidermal keratinocytes. The endpoint of this assay is direct detection array analyzed by the Meso Scale Discovery system SECTOR 2400 Imager. The Imager 2400 was used to detect and calculate the amount of a CGRP present in a sample. A similar procedure to that used in the Inhibition of Pro-Inflammatory Cytokines assay above was used to find that a 1% hydrolyzed algin blend inhibits CGRP production in primary adult human keratinocytes (Cascade # C-005-5C). An average inhibition of 65.70% over control was seen.

Antioxidative Properties

A blend of Escin, *Ruscus aculeatus* root extract, *Centella asiatica* extract, Hydrolyzed yeast protein, *Calendula officinalis* flower extract, and Ammonium glycyrrhizate was found to have antioxidative properties using the Oxygen Radical Absorption Capacity (ORAC) assay (Zen-Bio ORAC Anti-oxidant Assay kit (# AOX-2)). This assay measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner. A summary of these data are provided in Table 2.

TABLE 2*

| Blend Amount | % Better than 100 μM Trolox | % Better than Untreated |
| --- | --- | --- |
| 0.1% | 201.31 | 276.21 |
| 0.01% | 48.69 | 136.31 |
| 0.001% | −73.80 | 24.02 |

*Blend of Escin, *Ruscus aculeatus* root extract, *Centella asiatica* extract, Hydrolyzed yeast protein, *Calendula officinalis* flower extract, and Ammonium glycyrrhizate used was Biophytex™ LS 9832 and can be obtained from BASF Care Creations.

The procedure used to obtain the data in Table 2 included the following steps:

Step 1: Warm the plate reader incubation chamber to 37° C. Set-up plate reader to perform a kinetic read for 30 minutes with 1 minute intervals. Excitation=480 nm; Emission=520 nm.

Step 2: Prepare fluorescein working solution from the stock solution provided by transferring 16.8ml of Assay Buffer to an empty tube (not provided) and adding 1.2 ml stock fluorescein solution. Mix and protect from light.

Step 3: Prepare Trolox standards as follows: Briefly spin down the contents of the 1.5 mM Trolox standard tube after thawing. Pipette 580 μl of Assay Buffer into the 1.5 mM Trolox standard tube provided and mix well by vortexing. This produces a diluted stock Trolox standard of 50 M. Pipette 50 μl of assay buffer into 6 tubes. Using the newly diluted stock Trolox solution, prepare a dilution series. Mix each new dilution thoroughly before proceeding to the next. The 50 M stock dilution serves as the highest standard, and the assay buffer serves as the zero standard.

Step 4: Add 150 μl of the working fluorescein solution to each well of the assay plate provided.

Step 5: Add 25 μl of samples or Trolox standards to individual wells of the assay plate provided, add 25 μl of assay buffer to individual wells as a negative control. Place plate at 37° C. for at least 5 minutes.

Step 6: While the assay plate is equilibrating to 37° C., prepare the AAPH Working Solution by adding 2.7 ml Assay Buffer to the tube provided and gently invert. Place the working solution on ice until needed. AAPH solution is good for 8 hours if kept on ice.

Step 7: To begin the assay, add 25 μl of the AAPH working solution to each of the wells containing standards and samples from step 5. Place the assay plate in the plate reader and begin kinetic fluorescence reading.

Example 2

Formulations

Formulations having the ingredients from Example 1 were prepared as a freshener/toner (Table 3), mask (Table 4), and gel (Table 5 and Table 6).

TABLE 3*

| Ingredient | % Concentration (by weight) |
| --- | --- |
| Water | 88 |
| Butylene glycol | 6 |
| Glycerin | 4.5 |
| Propylene glycol | 0.56 |
| Diazolidinyl urea | 0.3 |
| PPG-5-Ceteth-20 | 0.17 |
| Methylparaben | 0.11 |
| Sodium citrate | 0.07 |
| Disodium EDTA | 0.05 |
| Buteth-3 | 0.04 |
| Propylparaben | 0.03 |
| Citric acid | 0.02 |
| Sodium benzotriazolyl butylphenol sulfonate | 0.02 |
| Panthenol | 0.01 |
| Hydrolyzed algin | 0.007 |
| Escin | 0.003 |
| *Ruscus aculeatus* root extract | 0.0015 |
| Ammonium glycyrrhizate | 0.001 |
| *Centella asiatica* extract | 0.00065 |
| Hydrolyzed yeast protein | 0.0004 |
| *Calendula officinalis* flower extract | 0.00035 |
| Excipients** | q.s. |

*Formulation can be prepared by mixing the ingredients in a beaker under heat 70-75° C. until homogenous. Subsequently, the formulation can be cooled to standing room temperature (20-25° C.).
**Excipients were added to modify the rheological properties of the composition. Alternatively, the amount of water can be varied so long as the amount of water in the composition is at least 80% w/w, and preferably between 80 to 90% w/w.

TABLE 4*

| Ingredient | % Concentration (by weight) |
|---|---|
| Water | 84 |
| Pentylene glycol | 5 |
| Polysilicone-11 | 2.9 |
| Hydroxyethyl acrylate/sodium acryloyldimethyl taurate copolymer | 1.9 |
| Dimethicone | 1.4 |
| Squalane | 1.3 |
| Glyceryl undecylenate | 1 |
| Silica | 0.5 |
| Acrylates/C10-30 alkyl acrylate crosspolymer | 0.45 |
| Butylene glycol | 0.35 |
| Triethanolamine | 0.35 |
| Polysorbate 60 | 0.28 |
| Hydroxypropyl cyclodextrin | 0.08 |
| Sorbitan isostearate | 0.08 |
| Panthenol | 0.05 |
| Hydrolyzed algin | 0.035 |
| Glycerin | 0.03 |
| Escin | 0.015 |
| *Ruscus aculeatus* root extract | 0.0075 |
| Ammonium glycyrrhizate | 0.005 |
| *Centella asiatica* extract | 0.00325 |
| Hydrolyzed yeast protein | 0.002 |
| *Calendula officinalis* flower extract | 0.00175 |
| Excipients** | q.s. |

*Formulation can be prepared by mixing the ingredients in a beaker under heat 70-75° C. until homogenous. Subsequently, the formulation can be cooled to standing room temperature (20-25° C.).
**Excipients were added to modify the rheological properties of the composition. Alternatively, the amount of water can be varied so long as the amount of water in the composition is at least 80% w/w, and preferably between 80 to 90% w/w.

TABLE 5*

| Ingredient | % Concentration (by weight) |
|---|---|
| Water | 86 |
| Glycerin | 5.4 |
| Pentylene glycol | 4 |
| Glycereth-26 | 2 |
| Propylene glycol | 0.56 |
| Triethanolamine | 0.55 |
| Acrylates/C10-30 alkyl acrylate crosspolymer | 0.3 |
| Diazolidinyl urea | 0.3 |
| Hydroxyethylcellulose | 0.2 |
| Sodium polyacrylate | 0.15 |
| Methylparaben | 0.11 |
| Disodium EDTA | 0.1 |
| Butylene glycol | 0.07 |
| Phenoxyethanol | 0.05 |
| Caprylyl glycol | 0.05 |
| Propylparaben | 0.03 |
| Panthenol | 0.01 |
| Hydrolyzed algin | 0.007 |
| Escin | 0.003 |
| *Ruscus aculeatus* root extract | 0.0015 |
| Ammonium glycyrrhizate | 0.001 |
| *Centella asiatica* extract | 0.00065 |
| Hydrolyzed yeast protein | 0.0004 |
| *Calendula officinalis* flower extract | 0.00035 |
| Excipients** | q.s. |

*Formulation can be prepared by mixing the ingredients in a beaker under heat 70-75° C. until homogenous. Subsequently, the formulation can be cooled to standing room temperature (20-25° C.).
**Excipients were added to modify the rheological properties of the composition. Alternatively, the amount of water can be varied so long as the amount of water in the composition is at least 80% w/w, and preferably between 80 to 90% w/w.

TABLE 6*

| Ingredient | % Concentration (by weight) |
|---|---|
| Water | 86 |
| Glycerin | 5.4 |
| Pentylene glycol | 4 |
| Glycereth-26 | 2 |
| Benzyl Alcohol | 0.9 |
| Triethanolamine | 0.55 |
| Acrylates/C10-30 alkyl acrylate crosspolymer | 0.3 |
| Hydroxyethylcellulose | 0.2 |
| Sodium polyacrylate | 0.15 |
| Disodium EDTA | 0.1 |
| Hydroxypropyl cyclodextrin | 0.08 |
| Butylene glycol | 0.07 |
| Phenoxyethanol | 0.05 |
| Caprylyl glycol | 0.05 |
| Panthenol | 0.01 |
| Hydrolyzed algin | 0.007 |
| Escin | 0.003 |
| *Ruscus aculeatus* root extract | 0.0015 |
| Ammonium glycyrrhizate | 0.001 |
| *Centella asiatica* extract | 0.00065 |
| Hydrolyzed yeast protein | 0.0004 |
| *Calendula officinalis* flower extract | 0.00035 |
| Excipients** | q.s. |

*Formulation can be prepared by mixing the ingredients in a beaker under heat 70-75° C. until homogenous. Subsequently, the formulation can be cooled to standing room temperature (20-25° C.).
**Excipients were added to modify the rheological properties of the composition. Alternatively, the amount of water can be varied so long as the amount of water in the composition is at least 80% w/w, and preferably between 80 to 90% w/w.

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A method of treating dry skin of a human, or flaky skin of a human, or a combination of dry and flaky skin of a human, the method comprising topically applying to the skin of the human in need thereof a composition comprising a therapeutically effective amount of:
   (a) hydrolyzed algin;
   (b) escin;
   (c) *Ruscus aculeatus* root extract;
   (d) ammonium glycyrrhizate;
   (e) *Centella asiatica* extract;
   (f) hydrolyzed yeast protein; and
   (g) *Calendula officinalis* flower extract,
wherein topical application of the composition to the skin reduces dryness of the skin, or reduces flakiness of the skin, or reduces a combination of dryness and flakiness of the skin.

2. The method of claim 1, wherein the skin comprises dry skin and topical application of the composition to the skin reduces dryness of the skin.

3. The method of claim 1, wherein the skin comprises flaky skin and topical application of the composition to the skin reduces flakiness of the skin.

4. The method of claim 1, wherein the composition is an emulsion.

5. The method of claim 4, wherein the emulsion is an oil-in-water emulsion.

6. The method of claim 1, wherein the composition is a lotion or a cream.

7. The method of claim 1, wherein the composition is a gel.

8. The method of claim 1, wherein the composition further comprises 80 to 90% by weight of water.

9. The method of claim 1, wherein the composition comprises:
   (a) 0.0001% to 1% by weight of hydrolyzed algin;
   (b) 0.0001% to 1% by weight of escin;
   (c) 0.0001% to 1% by weight of *Ruscus aculeatus* root extract;
   (d) 0.0001% to 1% by weight of ammonium glycyrrhizate;
   (e) 0.0001% to 1% by weight of *Centella asiatica* extract;
   (f) 0.0001% to 1% by weight of hydrolyzed yeast protein; and
   (g) 0.0001% to 1% by weight of *Calendula officinalis* flower extract.

10. The method of claim 1, wherein the composition further comprises butylene glycol; glycerin; propylene glycol; diazolidinyl urea; PPG-5-ceteth-20; methylparaben; sodium citrate; disodium EDTA; buteth-3; propylparaben; citric acid; sodium benzotriazolyl butylphenol sulfonate; and panthenol.

11. The method of claim 1, wherein the composition further comprises glycerin; pentylene glycol; glycereth-26; propylene glycol; triethanolamine; acrylates/C 10-30 alkyl acrylate crosspolymer; diazolidinyl urea; hydroxy ethylcellulose; sodium polyacrylate; methylparaben; disodium EDTA; butylene glycol; phenoxy ethanol; caprylyl glycol; propylparaben; and panthenol.

12. The method of claim 1, wherein the composition further comprises pentylene glycol; polysilicone-11; hydroxyethyl acrylate/sodium acryloyldimethyl taurate copolymer; dimethicone; squalane; glyceryl undecylenate; silica; butylene glycol; triethanolamine; polysorbate 60; acrylates/C 10-30 alkyl acrylate crosspolymer; hydroxypropyl cyclodextrin; sorbitan isostearate; panthenol; and glycerin.

13. The method of claim 1, wherein the composition further comprises glycerin; pentylene glycol; glycereth-26; benzyl alcohol; triethanolamine; acrylates/C 10-30 alkyl acrylate crosspolymer; hydroxy ethylcellulose; sodium polyacrylate; di sodium EDTA; hydroxypropyl cyclodextrin; butylene glycol; phenoxy ethanol; caprylyl glycol; and panthenol.

14. The method of claim 1, wherein the skin comprises dry skin and flaky skin and topical application of the composition to the skin reduces dryness and flakiness of the skin.

\* \* \* \* \*